(12) United States Patent
Serrero

(10) Patent No.: US 7,651,854 B2
(45) Date of Patent: Jan. 26, 2010

(54) METHODS FOR INCREASING THE PROLIFERATION OF B CELLS

(75) Inventor: Ginette Serrero, Columbia, MD (US)

(73) Assignee: A & G Pharmaceutical, Inc., Columbia, MD (US)

( * ) Notice: Subject to any disclaimer, the term of this patent is extended or adjusted under 35 U.S.C. 154(b) by 305 days.

(21) Appl. No.: 10/546,868

(22) PCT Filed: Dec. 17, 2003

(86) PCT No.: PCT/US03/40111

§ 371 (c)(1),
(2), (4) Date: May 30, 2006

(87) PCT Pub. No.: WO2004/078782

PCT Pub. Date: Sep. 16, 2004

(65) Prior Publication Data

US 2007/0015225 A1 Jan. 18, 2007

Related U.S. Application Data

(60) Provisional application No. 60/449,593, filed on Feb. 26, 2003.

(51) Int. Cl.
| | |
|---|---|
| C12N 5/06 | (2006.01) |
| C12N 5/08 | (2006.01) |
| C12N 5/12 | (2006.01) |
| A61K 39/395 | (2006.01) |
| C07K 16/00 | (2006.01) |
| C12P 21/08 | (2006.01) |

(52) U.S. Cl. .......... 435/326; 435/346; 435/355; 435/372.2; 435/384; 424/130.1; 424/141.1; 530/387.1; 530/388.1

(58) Field of Classification Search .......... None
See application file for complete search history.

(56) References Cited

U.S. PATENT DOCUMENTS

| | | | |
|---|---|---|---|
| 5,416,192 | A | 5/1995 | Shoyab et al. |
| 6,309,826 | B1 | 10/2001 | Serrero |
| 6,511,986 | B2 | 1/2003 | Zhang et al. |
| 6,670,183 | B2 | 12/2003 | Serrero |
| 6,720,159 | B1 | 4/2004 | Serrero |
| 6,824,775 | B2 | 11/2004 | Serrero |
| 7,368,428 | B2 | 2/2005 | Serrero |
| 6,881,548 | B2 | 4/2005 | Serrero |
| 7,091,047 | B2 | 8/2006 | Serrero |
| 7,411,045 | B2 | 8/2008 | Serrero et al. |
| 2002/0094966 | A1 | 7/2002 | Serrero |
| 2003/0092661 | A1 | 5/2003 | Serrero |
| 2003/0215445 | A1 | 11/2003 | Serrero |
| 2004/0131618 | A1 | 7/2004 | Serrero |
| 2005/0106150 | A1 | 5/2005 | Serrero |
| 2007/0015225 | A1 | 1/2007 | Serrero |
| 2008/0114070 | A1 | 5/2008 | Serrero |
| 2008/0145369 | A1 | 6/2008 | Serrero |
| 2008/0311120 | A1 | 12/2008 | Serrero et al. |
| 2009/0010931 | A1 | 1/2009 | Serrero |

FOREIGN PATENT DOCUMENTS

| | | |
|---|---|---|
| WO | WO-9115510 | 10/1991 |
| WO | WO-93/15195 | 8/1993 |
| WO | WO-02/31198 | 4/2002 |
| WO | WO-2002102306 | 12/2002 |
| WO | WO-2004045544 | 6/2004 |
| WO | WO-2005/000207 | 1/2005 |

OTHER PUBLICATIONS

He et al. Cancer Research, 62:5590-5596, Oct. 1, 2002.*
Wang et al. Clinical Cancer Research, 12(1):49-56, 2006.*
Campbell et al. Biology, 5th ed. p. 856, 1999.*
Zanocco-Marani T et al: "Biological activities and signaling pathways of the granulin/epithelin precursor." Cancer Research. Oct. 15, 1999, vol. 59, No. 20, pp. 5331-5340, XP002376335 ISSN: 0008-5472.
Bhandari V et al: "Isolation and Sequence of the Granulin Precursor CDNA from Human Bone Marrow Revelas Tandem Cysteine-Rich Granulin Domains" Proceedings of the Ntional Academy of Science, Washington, DC, US, vol. 89, Mar. 1992, pp. 1715-1719, XP002913828 ISSN: 0027-8424.
Daniel Rachael et al: "Cellular localization of gene expression for progranulin" Journal of Histochemistry and Cytochemistry, vol. 48, No. 7, Jul. 2000, pp. 999-1009, XP0023763336 ISN: 0022-1554 p. 1002, col. 2, para. 4, p. 1004, col. 2; p. 1007, col. 2, para. 2, p. 1008, col. 1, para. 1.
Wang, et al., "PC Cell-derived Growth Factor (Granulin Precursor) Expression and Action in Human Multiple Myeloma[1]" Clinical Cancer Research, vol. 9, pp. 2221-2228, Jun. 2003.

(Continued)

Primary Examiner—David J. Blanchard
(74) Attorney, Agent, or Firm—Womble Carlyle Sandridge & Rice, PLLC

(57) ABSTRACT

Disclosed herein are methods of increasing the proliferation of non-tumorigenic B cells. The methods involve administering PCDGF and optionally other B cells stimulators (e.g., IgM, LPS) to B cells resulting in an increase in B cell proliferation. The methods of the invention can be used, for example, to establish B cells lines, to sort B cells from a mixed population of cells, or to activate resting B cells.

8 Claims, 9 Drawing Sheets

OTHER PUBLICATIONS

J. Barnwell et al., "A Human 88-kD Membrane Glycoprotein (CD36) functions in vitro as a receptor for a cytoadherence ligand on plasmodium falciparum-infected erythrocytes," J. Clin. Invest., Sep. 1989, vol. 84, pp. 765-772.

A. Bateman et al., "Granulins, A Novel Class of Peptide from Leukocytes," Biochemical and Bioah sical Research Communications, vol. 173, No. 3, 1990, pp. 1161-1168.

R. Daniel, et al., "Cellular localization of Gene Expression for Progranulin," Journal of Histochemistry and Cyochemistry, Jul. 2000, vol. 48, No. 7, pp. 999-1009.

Hoque, et al., "The growth factor granulin interacts with cyclin T1 and modulates P-TEfb-dependent transcription," Mol Cell Biol., Mar. 2003, vol. 23, No. 5, pp. 1688-1702.

MB Jones et al., "The granulin-epithelin precursor/PC-cell-derived growth factor is a growth factor for epithelial ovarian cancer," Clin Cancer Res., Jan. 2003, vol. 9, No. 1, pp. 44-51.

C. Landry et al., "Expression of oligodendrocytic mRNAs in glial tumors: changes associated with tumor grade and extent of neoplastic infiltration1," Cancer Research, Sep. 15, 1997, vol. 57, pp. 4098-4104.

R. Lu et al., "Mediation of estrogen mitogenic effect in human breast cancer MCF-7 cells by PC-cell-derived growth factor (PCDGF/granulin precursor)," Proc Natl Acad Sci USA, Jan. 2, 2001, vol. 98, No. 1, pp. 142-147.

R. Lu et al., "Inhibition of PC-cell-derived growth factor (PCDGF, epithelin/granulin precursor) expression by antisense PCDGF cDNA transfection inhibits tumorigenicity of the human breast carcinoma cell line MDA-MB-468," Proc Natl Acad Sci USA, Apr. 11, 2000, vol. 97, No. 8, pp. 3993-3998.

R. Lu et al., "Stimulation of PC cell-derived growth factor (epithelin/granulin precursor) expression by estradiol in human breast cancer cells," Biochem Biophys Res Commun., Mar. 5, 1999, vol. 256, No. 1, pp. 204-207.

G. Plowman et al., "The Epithelin Precursor Encodes Two Proteins with Opposing Activities on Epithelial Cell Growth," The Journal of Biological Chemistry, vol. 267, No. 18, 1992, pp. 13073-13078.

G. Serrero, "Expression of PC cell-derived growth factor in benign and malignant human breast epithelium," Hum Pathol., Nov. 2003, vol. 34, No. 11, pp. 1148-1154.

G. Serrero, "Autocrine growth factor revisited: PC-cell-derived growth factor (progranulin), a critical player in breast cancer tumorigenesis," Biochem Biophys Res Commun., Aug. 29, 2003, vol. 3, pp. 409-413.

H. E. Turner et al., "Expression analysis of cyclins in pituitary adenomas and the normal pituitary gland," Clinical Endocrinology, (2000), vol. 53, pp. 337-344.

L. Liau et al., "Identification of a human glioma-associated growth factor gene, *granulin*, using differential immuno-absorption1," Cancer Research, Mar. 1, 2000, vol. 60, pp. 1353-1360.

S. Lee et al., "Enhanced sensitization to taxol-induced apoptosis by herceptin pretreatment in ErbB2-overexpressing breast cancer cells1," Cancer Research, Oct. 15, 2002, vol. 62, pp. 5703-5710.

W. Wang et al., "PC-Cell Derived Growth Factor (PCDG, progranulin) Expression and Action in Human Multiple Myelomas," Proceedings of American Association for Cancer Research, Mar. 2001, vol. 42, pp. 835, XP-001248624, Abstract.

X. Xia et al., "Identification of cell surface binding sites for PC cell-derived growth factor, PCDGF, (epithelin/granulin precursor) on epithelial cells and fibroblasts," Biochem Biophys Res Commun, Apr. 17, 1998, vol. 245, No. 2, pp. 539-543.

H. Zhang et al., "Inhibition of tumorigenicity of the teratoma PC cell line by transfection with antisense cDNA for PC cell-derived growth factor (PCDGF, epithelin/granulin precursor)," Proc Natl Acad Sci USA Nov. 24, 1998, vol. 95, No. 24, pp. 14202-14207.

J. Zhou et al., "Purification of an Autocrine Growth Factor Homologous with Mouse Epithelin Precursor from a Highly Tumorigenic Cell Line," The Journal of Biological Chemistry, vol. 268, No. 15, 1993, pp. 10863-10869.

\* cited by examiner

|  | 24 hours | 48 hours | 72 hours |
|---|---|---|---|
| Con | 511±111 | 474±83 | 127±6 |
| 10µg/ml LPS | 11635±297 | 51215±1386 | 14314±1054 |
| Fold Stimulation | 23 | 108 | 113 |

FIG.3

|  | Con | LPS | ConA |
|---|---|---|---|
| CPM | 722±55 | 57845±3632 | 25668±1400 |
| Fold Stimulation | 1.0 | 80.1 | 35.6 |

FIG.6

FIG.8C
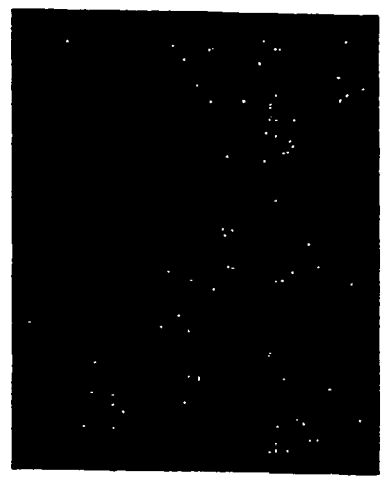
FIG.8F
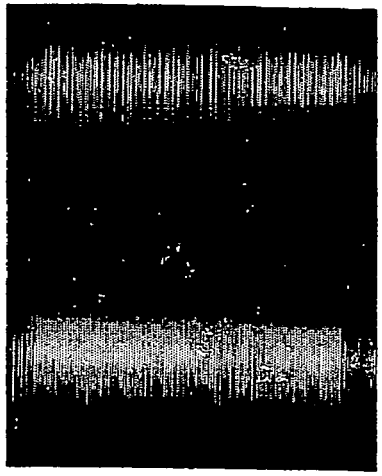
FIG.8B
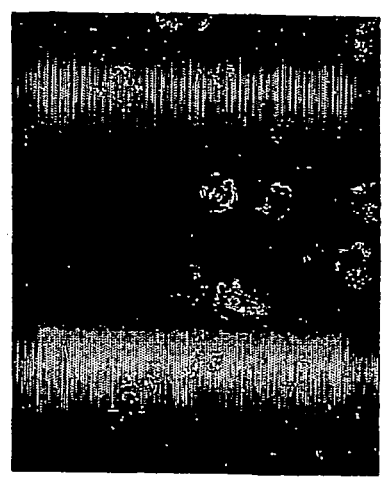
FIG.8E
FIG.8A
FIG.8D

METHODS FOR INCREASING THE
PROLIFERATION OF B CELLS

CROSS REFERENCE TO RELATED APPLICATIONS

The present application is a United States national stage application of PCT/US03/40111, filed Dec. 17, 2003, which claims benefit of U.S. application Ser. No. 60/449,593, Feb. 26, 2003.

REFERENCES

Several publications are referenced herein. Full citations for these publications are provided below. The disclosures of these publications are hereby incorporated herein by reference in their entirety, unless otherwise noted.

BACKGROUND OF THE INVENTION

The proliferation and differentiation of cells in multicellular organisms is subject to a highly regulated process. A distinguishing feature of cancer cells is the absence of control over this process; proliferation and differentiation become deregulated resulting in uncontrolled growth. Significant research efforts have been directed toward better understanding this difference between normal and tumor cells. One area of research focus is growth factors and, more specifically, autocrine growth stimulation.

Growth factors are polypeptides which carry messages to cells concerning growth, differentiation, migration and gene expression. Typically, growth factors are produced in one cell and act on another cell to stimulate proliferation. However, certain malignant cells, in culture, demonstrate a greater or absolute reliance on an autocrine growth mechanism. Malignant cells which observe this autocrine behavior circumvent the regulation of growth factor production by other cells and are therefore unregulated in their growth.

B cell development is composed of two phases: antigen independent and antigen dependent. The antigen-independent phase of B cell development occurs in the bone marrow where B cell progenitors differentiate into immature B cells expressing cell surface IgM. The antigen-dependent phase of B cells differentiation occurs in the peripheral secondary lymphoid organs where antigen-specific B cells proliferate and differentiate into plasma cells that secrete specific antibody upon activation.

During the antigen-independent phase of B cell development, sequential rearrangement of immunoglobulin gene segments generates a diverse repertoire of antigens. Pro-B cells, the earliest B-lineage cells derived from B cell progenitors, are characterized by the appearance of early B-cell lineage cell-surface proteins and by immunoglobulin gene rearrangement of the heavy-chain locus. The pro-B cell stage is followed by pre-B cell stage which is characterized by the rearrangement of the immunoglobulin light chain gene. Successful rearrangement of both heavy and light chains leads to the expression of intact IgM molecules on the cell surface at the immature B cell stage.

Immature B cells undergo selection for self-tolerance in a series of checkpoints triggered by antigens and selection for the ability to survive in the peripheral lymphoid tissues. B cells that survive the selection for self-tolerance and the ability to survive in the peripheral lymphoid tissues further differentiate to become mature B cells that express surface IgD in addition to surface IgM [Burrows, 1997]. Mature B cells recirculate through peripheral lymphoid tissues where they may encounter antigens. B cells activated by antigen may differentiate into plasma cells and secrete a large amount of antibodies [Duchosal, 1997]. There are 5 different classes of immunoglobulin molecule: IgM, IgD, IgG, IgA, and IgE. IgM is the first immunoglobulin molecule to be synthesized and expressed.

Antigen dependent B cell development and differentiation begin with the binding of antigens on B cells. B cell activation requires two signals: binding of the antigen to the B-cell surface immunoglobulin and interaction of B cells with antigen-specific helper T cells. The surface immunoglobulin serving as the B-cell antigen receptor (BCR) has an important role in B-cell activation. After binding the antigen, the BCR and antigen complex is internalized and the antigen protein is degraded. The digested antigen returns to the B-cell surface as peptides bound to MHC class II molecules [Parker, 1993].

As B cells develop from pro B cells to plasma cells, they express cell surface proteins other than immunoglobulin that are useful markers for B-lineage cells at different developmental stages. One of the first identifiable proteins expressed on the surface of B-lineage cells is CD45R (also known as B220) [Osmond, 1998; Hardy, 2001]. CD45R, a protein tyrosine phosphatase that functions in B-cell receptor signaling, is expressed throughout B-cell development from pro-B cells right up to plasma cells [Osmond, 1998; Hardy, 2001]. CD43 (the mucin leukosialin) is also expressed at the pro-B cell stage but its expression is lost as cells progress to immature B cells [Hardy, 2001]. CD43 is a multi-functional molecule with directly contradictory functionality [Ostberg, 1998]. For example, CD43 can act as an adhesion molecule that may guide cell-cell interactions of B-cell precursors with stromal cells [Ostberg, 1998]. However, CD43 also has anti-adhesion functions [Ostberg, 1998]. CD43 has an important role in cell signaling and cytoskeletal interaction [Ostberg, 1998]. CD19 is another surface marker protein expressed from pro-B cells through the plasma cell stage [Hardy, 2001]. CD19 is involved in B-cell receptor signaling and lowers the threshold for antigen receptor stimulation of B cells [LeBien, 1998]. Other cell-surface molecules expressed during different stages of B-cell development include the heat-stable antigen HSA, CD 10, CD 20, CD 22, CD38, and CD40 [Duchosal, 1997; Hardy, 2001].

B cell development and differentiation of antigen independent phase are tightly regulated by lineage and stage specific growth factors and cell adhesion molecules. Interleukin 7 (IL-7), secreted by stromal cells, is an essential growth factor for early B cell development. IL-7 can stimulate pro and pre B cell proliferation [Duchosal, 1997]. Neutralizing anti-IL-7 antibody can inhibit IL-7 induced proliferation of pro- and pre-B cells [Duchosal, 1997]. IL-7 dependent pro-B cell proliferation is potentiated by insulin like growth factor-I and stem cell factor, two stromal growth factors [Duchosal, 1997]. Interferons (IFNs)-α/β, secreted by macrophages in bone marrow, can inhibit IL-7 induced B cell growth through apoptosis [Burrows, 1997]. The stromal cell-derived factor 1 or pre-B cell growth-stimulating factor (SDF-1/PBSF), produced constitutively by bone marrow stromal cells, stimulates proliferation of pro and pre-B cells [Nagasawa, 1996]. In vivo experiments show that mice lacking PBSF/SDF-1 died perinatally [Nagasawa, 1996]. IL-3 stimulates pre-B cell proliferation through the interaction with IL-3 receptor on B cells. [Duchosal, 1997]. IL-3 is a T cell derived cytokine and together with IL-6, can stimulate multipotential stem cells and B cell progenitor [Kincade, 1989]. Neuroleukin, a glucose-6-phosphate isomer homolog, has the ability to stimulate B cell development [Kincade, 1989].

There are several growth factors that negatively regulate B cell development. IL-1 inhibits generation of pre-B cells from earlier pro-B cells [Ryan, 1994]. However, IL-1 increases the generation of Ig secreting B cells from human bone marrow culture [Ryan, 1994]. TNF-α and IL-4 inhibit human lymphoid progenitor colonies [Ryan, 1994]. Cell adhesion molecules are also important for early B cell development. Stem cell factor (SCF), present on the cell surface of stromal cells, interacts with the cell-surface receptor tyrosine kinase, kit, on B cell precursor and stimulates early B cell development [Ashman, 1999]. SCF exists in both soluble and membrane bound form as a result of differential splicing and proteolytic cleavage [Ashman, 1999]. The membrane bound form of SCF contributes to its regulation of early B cell development [Ashman, 1999]. Flk2/flt3 is a receptor tyrosine kinase in the same family as the stem cell factor receptor c-kit. The flk2/flt3 ligand, which has homology to CSF-1, is a potent costimulator of early pro-B cells, in addition to IL-7 and SCF [Burrows, 1997]. Disruption of the flk2/flt3 gene leads to a selective deficiency of primitive B cell progenitors [Burrows, 1997].

VLA-4 is a cell surface molecule of B-cell precursors that interacts with the extracellular matrix ligand fibronectin on stromal cells and macrophages, and VCAM-1 on endothelial cells and macrophages [Duchosal, 1997]. VLA-4 expresses more on pro-B cells than pre B cells. Therefore, VLA-4 modulates pro-B cell proliferation more effectively than pre-B cells [Duchosal, 1997].

The interaction between CD44 on B-cell precursors and hyaluronate on stromal cells also plays an important role in B cell development. Antibodies to CD44 inhibit mouse B cell development in vivo [Duchosal, 1997]. Hormones may also regulate B lymphopoiesis. Estrogen regulates B cell generation via an effect on stromal cells in the lymphopoietic microenvironment [Burrows, 1997]. Dwarf mice deficient in the expression of prolactin and thyroid-stimulating hormone are immunodeficient, due to a T cell deficiency and a defect in B cell development, which is correctable by the lack of thyroid hormone thyroxine [Burrows, 1997].

T helper cells transmit signals to B cells through a direct contact of the B cell and the helper T cell. This direct contact is accomplished by antigen independent interaction of accessory molecule, CD40 ligands on the T helper cell and CD40s on the B cell help T cells [Parker, 1993], and by antigen-specific interaction of the peptide:MHC class II complex on the B cell surface with antigen-specific T cell receptor on helper T cells. Antigen-mediated B cell activation occurs in a T cell-independent mode or a T cell-dependent mode. T cell-independent activation of B cells can occur in response to non-protein antigen, such as a polysaccharide. The ability of B cells to respond directly to polysaccharides provides a rapid response to many important bacterial pathogens [Vos, 2000]. T cell-dependent activation of B cells takes place in response to protein-antigens or to non-protein antigens conjugated to protein carrier molecules.

T-cell dependent activation of B cells is the core of humoral immunity. Activated helper T cells produce soluble cytokines that can stimulate B cell proliferation and differentiation [Parker, 1993]. The first identified soluble cytokine was IL-4, also known as B-cell stimulatory factor 1 (BSF-1) or B cell growth factor (BCGF). IL-4 was originally identified as a molecule able to stimulate DNA synthesis of anti-IgM-stimulated murine B lymphocytes [Howard, 1982]. Human IL-4 is a 153 amino acid glycoprotein having a protein core with a molecular mass of 15 KD. Glycosylated human IL-4 can have a molecular mass of 20 KD [Yokota, 1986; Ohara, 1987]. IL-4 has multiple effects on B cells. For example, IL-4 can enhance the proliferation of B cells stimulated with anti-IgM antibody [Howard, 1982], induce the expression of class II MHC expression and CD23 [Conrad, 1987; Jansen, 1990], and regulate immunoglobulin isotype expression. For example, IL-4 is able to induce B cells to produce IgE [Pene, 1988] and induce the switching of expression of cells from producing IgM to IgG1 and/or IgE [Callard, 1991]. IL-4 also plays a role in the regulation of T cells, mast cells, monocytes, hematopoiesis, fibroblasts, and NK cells [Jansen, 1990].

Interleukin-2 (IL-2) is a 133 amino acid glycoprotein with a molecule weight of 13 to 17.5 KD according to viable glycosylation [Robb, 1981]. IL-2, produced by T cells, stimulates the proliferation of activated B cells [Gearing, 1985], promotes the induction of immunoglobulin secretion and J chain synthesis by B cells [Gearing, 1985; Blackman, 1986], and acts to enhance immune effects mediated by activated B cells [Mingari, 1984].

Interleukin 6 (IL-6) is a 186 amino acid glycoprotein with a molecular weight of 19 to 30 KD [May, 1989] that is produced from many cell types including monocytes, macrophages, stromal cells, and plasma cells [May, 1988; Frassanito, 2001]. IL-6 is well established as a late-stage differentiation factor for B cell to plasma cell transition [Muraguchi, 1988]. IL-6 stimulates activated B cells to produce IgM, IgG, and IgA [Muraguchi, 1988]. IL-6 also augments antigen-specific antibody response to antigen in vitro and in vivo [Takatsuki, 1988]. While the antigen-dependent phase of T cell development depends on the production of an autocrine factor, IL-2, a corresponding autocrine regulatory factor for B cells has not yet been identified.

PCDGF (PC-cell derived growth factor) is a highly tumorigenic autocrine growth factor and causative agent for a wide variety of tumors. For example, PCDGF levels are elevated in tumorigenic hematopoetic cells such as B cell leukemias, but cannot be detected in normal B cells. As described in U.S. Pat. No. 6,309,826, incorporated by reference herein in its entirety, overexpression of PCDGF leads to uncontrolled tumor cell growth and increased tumorigenesis. The degree of PCDGF overexpression directly correlates with the degree of cellular tumorigenicity. Cells overexpressing PCDGF do not require external signals to maintain uncontrolled cell growth. Loss of regulated cell growth, such as a loss in responsiveness to insulin and/or estrogen, leads to increased malignancy and excessive unregulated cell growth. However, PCDGF has not previously been shown to be associated with stimulating the growth of non-tumorigenic (i.e., normal) B cells.

While PCDGF moderately increases the growth of 3T3 cells, PCDGF inhibits the growth of several other cell, lines. For example, PCDGF inhibits the growth of normal mink lung epithelial cells (CCL 64) cells. Xia, X and Serrero, G, Identification of cell surface binding sites for PC cell derived growth factor, (epithelin/granulin precursor) on epithelial cells and fibroblasts. Biochem. Biophys. Res. Commun. 245, 539-543, 1998. PCDGF also inhibits the growth of normal mouse and rat thymic epithelial cells (BT1B and TEA3A1 cells) (Serrero, unpublished results).

PCDGF has no effect on the proliferation of several normal human cell lines including Hela and CHO cells (Serrero, unpublished data), and Cos-7 cells (Plowman, et al, 1993; Serrero unpublished results; Plowman, G. D., Green, J. M., Neubauer, M. G., Buckley, S. D., McDonald, V. L., Todaro, G.

J., and Shoyab, M. (1992). The epithelin precursor encodes two proteins with opposing activities).

BRIEF SUMMARY OF THE INVENTION

The present invention provides methods of increasing the proliferation of non-tumorigenic B cells by administering PCDGF to B cells. We have discovered that PCDGF an autocrine growth factor for normal (i.e., non-tumorigenic) B cells. Thus, PCDGF can be used to increase proliferation of normal B cells for example, to improve the efficiency of primary hematopoietic cell culture. Improved efficiency and growth of primary B cell culture is of great value in, for example, establishing and maintaining cell lines (e.g., stem cell lines) for use in biomedical research.

The invention provides, in one embodiment, a method of increasing the proliferation of non-tumorigenic B cells by administering an effective amount of PCDGF to B cells wherein the proliferation of the B cells is increased by, preferably at least two-fold. Another embodiment of the invention provides a method of increasing the proliferation of non-tumorigenic B cells by administering an effective amount of PCDGF to B cells wherein the proliferation of the B cells is increased by at least three-fold. Further embodiments of the invention provide methods for stimulating DNA synthesis in non-tumorigenic B cells comprising administering PCDGF to B cells wherein DNA synthesis is increased by at least two-fold.

Additional embodiments and advantages of the present invention will be set forth in part in the description that follows, and in part will be obvious from the description, or may be learned through the practice of the invention. The objects and advantages of the invention will be attained by means of the instrumentalities and combinations particularly pointed out in the appended claims.

BRIEF DESCRIPTION OF THE DRAWINGS

FIG. 2A shows PCDGF staining in the absence of LPS while FIG. 2B shows PCDGF staining 48 hours after the addition of 10 ug/ml of LPS.

FIG. 3 shows that cell proliferation, as indicated by thymidine incorporation, increases by at least 100 fold after 48 hours incubation with 10 ug/ml of LPS.

FIG. 6 shows that cell proliferation of mouse spleen lymphocytes is activated by both LPS and Con A.

FIGS. 8A-F show that PCDGF positive cells are B lymphocytes. Mouse lymphocytes were stained with anti-B220-FITC antibody which is directed to B220 antigen, a common B cell marker. Cells that stained positive for PCDGF also stained positive for B220. Mouse spleen lymphocytes were incubated without LPS (8A-C) or with 10 ug/ml LPS (8D-F) and stained with B220-FITC antibody (8A and D), DAPI (8B and E) or anti-PCDGF antibody (8C and F).

DETAILED DESCRIPTION OF THE INVENTION

PCDGF is a potent growth factor for tumorigenic cells and the tumorigenic agent for a wide variety of tumors in breast, ovarian, lung, kidney, liver, hematopoietic and other tissues. Given PCDGF's prominent role in tumorigenesis, PCDGF research until now has been directed to inhibiting and/or inactivating PCDGF in order to inhibit or interfere with tumor cell growth. PCDGF antagonists, such as anti-PCDGF antibodies, interfere with the biological activity of PCDGF (e.g., tumorigenic activity) by binding PCDGF directly and preventing PCDGF from transmitting cell growth signals to a target cell (e.g., breast cancer cell). PCDGF has not previously been used to increase cellular proliferation in non-tumorigenic B cells.

The inventor has surprisingly found that PCDGF can be used to increase the proliferation of non-tumorigenic B cells. The term "non-tumorigenic B cells" refers to a B cells that do not exhibit the growth, regulatory, and/or biological activity of tumorigenic cell growth (e.g., unregulated growth, the ability to induce tumors after injection into an animal). The term "B cells" refers to B cells from any stage of development (e.g., B stem cells, progenitor B cells, differentiated B cells, plasma cells) and from any source including, but not limited to peripheral blood, lymph nodes, bone marrow, umbilical chord blood, or spleen cells.

Figure 1:
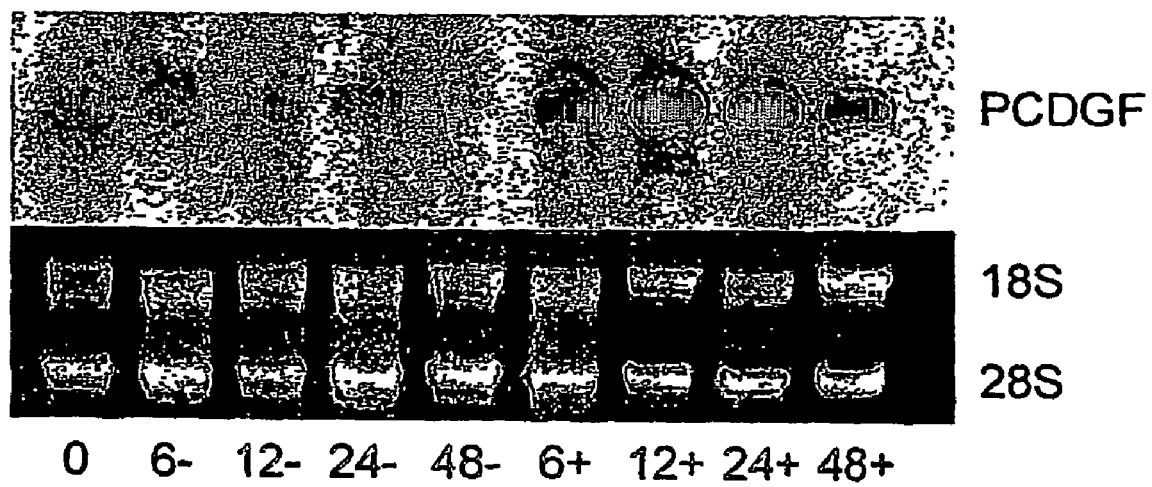
FIG. 1 shows that PCDGF mRNA levels in normal mouse B cells are dramatically increased upon activation of the cells from resting to activated state by the addition of LPS. PCDGF mRNA increased as early as six hours following addition of LPS (lipopolysaccharide) as shown by Northern blot analysis.

Although PCDGF is not detected in normal resting B cells (e.g., quiescent cells not undergoing cellular division or proliferation), PCDGF mRNA and protein levels are dramatically elevated when B cells are shifted from a resting to an active state. LPS (lipopolysaccharide) is a complex compound found in the cell wall of gram-negative bacteria. LPS is a known mitogen for B cells. When mouse spleen lymphocytes are activated with 10 ug/ml LPS, PCDGF mRNA expression increased as early as six hours post-treatment as shown by Northern blot analysis (FIG. 1). PCDGF mRNA is virtually undetectable in normal cells prior to the addition of LPS (see lanes 1-5 of FIG. 1). Six to forty-eight hours post-treatment with LPS, PCDGF mRNA expression increased dramatically (see lanes 6-9 of FIG. 1).

Figure 2A:
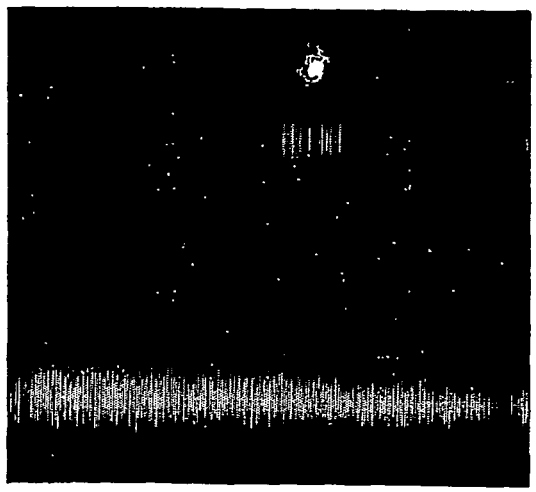
FIGS. 2A and 2B shows that PCDGF protein expression is also dramatically increased 48 hours after the addition of LPS as shown by immunofluorescent staining that detects the presence of PCDGF.
Figure 2B:
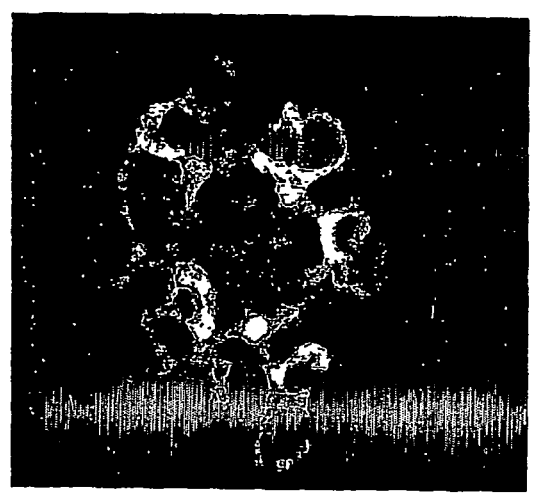

Activation of normal B cells with LPS also results in increased PCDGF protein expression. Immunofluorescent staining of mouse spleen lymphocytes with purified rabbit anti-human PCDGF antibody 48 hours after the addition of 10 ug/ml LPS (FIG. 2B) or control (FIG. 2A) shows the dramatic increase in PCDGF protein levels following treatment with LPS. Increased levels of PCDGF mRNA and protein correlates with increased cell proliferation (FIG. 3). Thymidine incorporation by mouse spleen lymphocytes was stimulated at least 100 fold after 48 hours of incubation with 10 ug/ml LPS.

Figure 4:
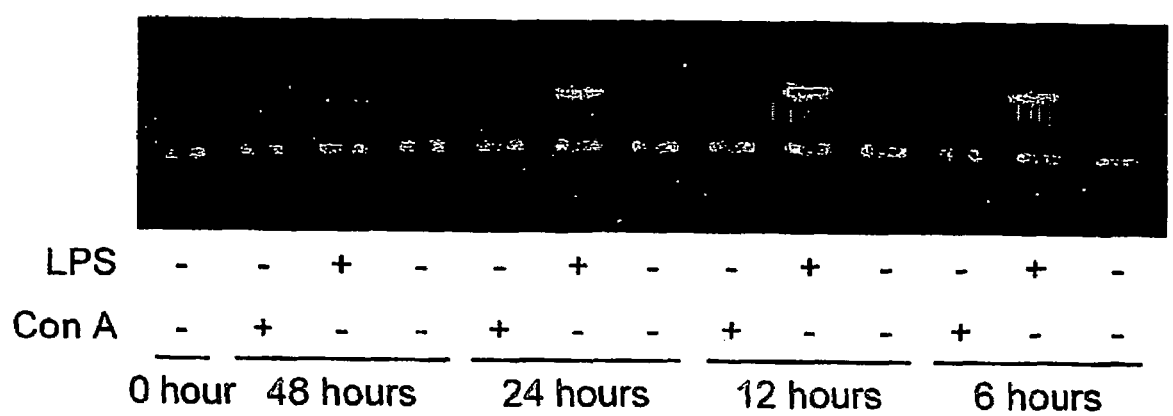
FIG. 4 shows that increased PCDGF expression was due to the addition of LPS. The reverse-transcriptase polymerase chain reaction (RT-PCR) assay shows that PCDGF mRNA was detected in LPS stimulated samples and not detected in the control or Con A stimulated samples.
Figure 5:
FIG. 5 shows that increased PCDGF protein expression was due to the addition of LPS since PCDGF protein was only detected in the LPS stimulated sample.

Mouse spleen lymphocytes are a mixture of B and T cells. In order to determine if LPS stimulation of mouse spleen lymphocytes is specific to B cells, Con A, a T lymphocyte activator, was used to activate mouse spleen lymphocytes. As shown in FIG. 4, PCDGF mRNA was only detected in LPS stimulated samples but not in the control or Con A stimulated samples as indicated in a reverse-transcriptase polymerase chain reaction (RT-PCR) experiment. PCDGF mRNA transcript is shown in the LPS+, Con A—lanes but not in the LPS−, Con A+ lanes between 6 and 48 hours after the addition of either LPS or Con A. Likewise, PCDGF protein levels are stimulated by LPS but not by Con A as shown by immunoprecipitation followed by Western blot analysis with anti-PCDGF antibody after 24 hours stimulation of mouse spleen lymphocytes with either 10 ug/ml LPS (FIG. 5, lane 2) or 2.5 ug/ml Con A (FIG. 5, lane 3). Proliferation of mouse spleen lymphocytes is stimulated by either 10 ug/ml LPS or 2.5 ug/ml Con A (FIG. 6). Thus, increased levels of PCDGF mRNA and protein in activated mouse spleen lymphocytes specifically results from the activation of B cells.

Figure 7A:
FIGS. 7A-D show that PCDGF positive cells are proliferating upon LPS stimulation. Mouse lymphocytes stimulated with LPS were immunostained using anti-PCDGF and anti-BrdU (thymidine analog antibody). Cells staining positive for PCDGF also stained positive for anti-BrdU and anti-B220 showing that the PCDGF positive cells stimulated with LPS were proliferating (i.e., incorporating thymidine). Mouse spleen lymphocytes were incubated without LPS (7A and B) or with 10 ug/ml LPS (7C and D) and stained with B220-BrDU antibody (7A and C) or anti-PCDGF antibody (7B and D).
Figure 7B:
Figure 7C:
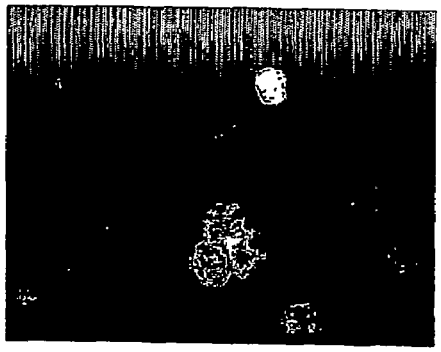
Figure 7D:
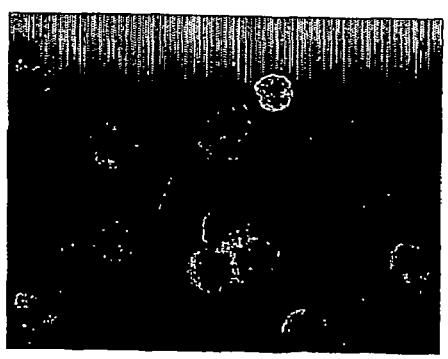

In order to determine if PCDGF positive mouse spleen lymphocytes are proliferating B cells upon LPS stimulation, immunofluorescent staining was carried out using antibodies directed to PCDGF, thymidine analog, and B cell markers. BrdU is a thymidine analog incorporated into DNA during DNA synthesis (an indicator of cell proliferation). B220 is an antigen, commonly used as a B cell marker, that is expressed on B lymphocytes at all stages from pro-B through mature B cells. Mouse spleen lymphocytes were incubated without (FIGS. 7A and 7B) or with (FIGS. 7C and 7D) 10 ug/ml LPS and stained with anti-BrdU antibodies (FIGS. 7A and 7C) or anti-PCDGF antibody (FIGS. 7B and 7D). As shown in FIGS. 7C and 7D, the PCDGF and LPS positive cells were also BrdU positive while the LPS negative cells were neither PCDGF or BrdU positive. Thus, the PCDGF positive cells were also proliferating B cells while the PCDGF negative cells (i.e., unstimulated cells) were not proliferating. The proliferating mouse spleen lymphocytes are B cells as shown in FIGS. 8A-8F. Mouse spleen lymphocytes were unstimulated (8A-C) or stimulated (8D-F) with 10 ug/ml LPS. The cells were stained with anti-B220 antibody (8A and 8D), DAPI (4,6-diamidino-2-phe-nylindole) nuclear stain (8B and 8E), or anti-PCDGF antibody (8C or 8F). The LPS stimulated cells were positive for B cell staining (anti-B220) and PCDGF staining (anti-PCDGF) as shown in FIGS. 8D and 8F. DAPI stains the nuclei of the cells and therefore shows the entire population of cells.

Figure 9:
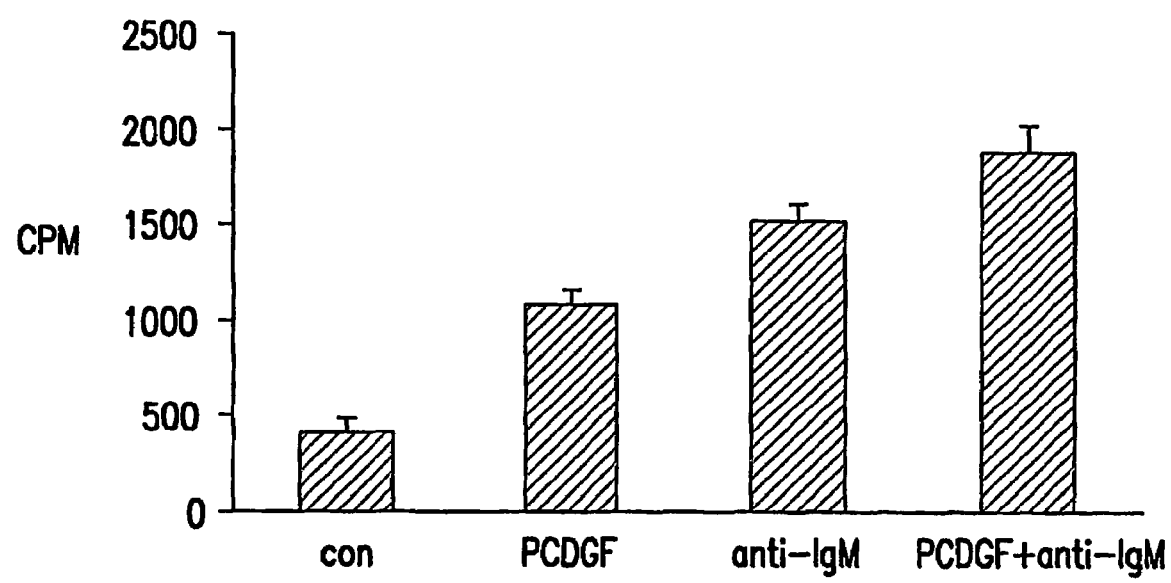
FIG. 9 shows that PCDGF stimulates mouse spleen cell proliferation. 200 ng/ml PCDGF, 10 ug/ml anti-IgM, and the combination of PCDGF and anti-IgM stimulated mouse resting B cell proliferation by 2.7, 3.7, and 4.6 fold respectively following a 72 hour treatment.

PCDGF can induce resting B cells to proliferate. As shown in FIG. 9, resting mouse spleen lymphocytes were treated with a control (lane 1), 200 ng/ml PCDGF (lane 2), 10 ug/ml IgM (lane 3), or both 200 ng/ml PCDGF and 10 ug/ml IgM (lane 4). B cell proliferation was stimulated after 72 hours treatment by 0, 2.7, 3.7, and 4.6 fold respectively in lanes 1-4. PCDGF alone (FIG. 9, lane 3) or in combination with IgM (FIG. 9, lane 4) can induce resting B cells to proliferate.

One embodiment of the invention provides methods of increasing the proliferation of non-tumorigenic B cells comprising administering an effective amount of PCDGF to said cells wherein the proliferation of said cells is increased by at least 2 fold. PCDGF can also be co-administered with another B cell proliferation factor including, but not limited to, IgM. Co-administration of PCDGF and another B cell mitogen (e.g., IgM, LPS) may further increase B cell proliferation as shown in FIG. 9. PCDGF and a co-B cell stimulator can be administered simultaneously or sequentially to B cells or incorporated directly into the B cell line media.

Another embodiment provides methods of increasing DNA synthesis in non-tumorigenic B cells comprising administering an effective amount of PCDGF to said cells wherein DNA synthesis in said cells is increased by, preferably at least 2 fold. A further embodiment of the invention provides methods of increasing DNA synthesis in non-tumorigenic B cells comprising administering an effective amount of PCDGF and another B cell DNA synthesis stimulating factor (e.g., IgM) to said cells wherein DNA synthesis in said cells is increased by, for example, at least 2 or 3 fold.

PCDGF can be provided to cells by adding PCDGF in an appropriate carrier (e.g., buffer) to cell culture medium at concentrations typically ranging from 0.01 ng to about 100 mg/ml and preferably from about 10 ng to about 50 mg/ml. B cells can also be transfected with DNA or RNA encoding PCDGF or active PCDGF fragments which retain the ability to increase proliferation of non-tumorigenic B cells or vectors containing such DNA or RNA sequences. Transfected B cells can be induced to make PCDGF or active PCDGF fragments using any suitable technique (e.g., inducible promoter, and multiple plasmid copies). In another embodiment of the invention, B cells can be co-localized with cells producing PCDGF (e.g., tumorigenic cells including, but not limited to, multiple myeloma cells, cells transfected with PCDGF encoding nucleic acid). PCDGF secreted from PCDGF-producing cells can induce proliferation of normal B cells in proximity to the PCDGF-producing cells.

A further embodiment of the invention provides methods of identifying proliferating B cells in a population of hematopoietic cells comprising, measuring the level PCDGF in said cells wherein cells expressing PCDGF are proliferating B cells. As shown in FIG. 8, PCDGF positive cells in a population of mouse spleen lymphocytes (including both B cells and T cells) also stain positive for proliferating B cells. Thus, positive staining for PCDGF is indicative of the presence of proliferating B cells in a population of hematopoietic cells. Proliferating B cells can be isolated from a mixed cell population and used to establish cell lines, form hybridomas with myeloma cells, or karyotyping.

B cells, and other hematopoietic cells, are generally known to be difficult to maintain in cell culture. PCDGF can be used to establish in vitro culture of mammalian B cells from any source (e.g., stem cells, bone marrow, umbilical cord blood, embryonic stem cells). Another embodiment of the invention provides methods of increasing the proliferation of non-tumorigenic PCDGF-responsive cells (e.g., mammalian B-cells, mammalian B stem cells, mammalian bone marrow cells, and PCDGF-responsive cells of hematopoietic systems, embryonic stem cells). For example, PCDGF can be used to stimulate the formation of hybridoma cells which are formed from fused spleen cells and multiple myeloma cells.

In further embodiments of the invention, PCDGF can be used to establish and maintain immortalized B-cell lines, expand B cell populations for karyotyping, and to stimulate antigen production from resting B cells. B cells from any stage of B cell development or any source can be activated using PCDGF and/or a co-B cell stimulator, identified using anti-PCDGF antibodies, and established in an in vitro cell lines. B cell lines can be immortalized and/or maintained in a proliferating and active state by the addition of PCDGF to the cell culture media. PCDGF can also be used to activate resting B cells resulting in the production of antibodies. For example, PCDGF can be used to stimulate the formation of hybridoma cells which are formed from fused spleen cells and multiple myeloma cells.

It is to be understood that application of the teachings of the present invention to a specific problem or environment will be within the capability of one having ordinary skill in the art in light of the teachings contained herein. The present invention is more fully illustrated by the following non-limiting examples.

EXAMPLE 1

LPS Stimulated PCDGF Expression

We investigated the expression of PCDGF upon activation by LPS, a mitogen for mouse normal B cells. When mouse spleen lymphocytes were activated by 10 μg/ml ml LPS, PCDGF mRNA expression was dramatically increased as early as 6 hours as shown by Northern blot analysis (FIG. 1). Mouse spleen lymphocytes were cultured at $1.2 \times 10^6$ cells/ml in RPMI 1640 containing 10% PBS. 10 μg/ml LPS was used to activate resting mouse B cells. RNAs were isolated at 0, 6, 12, 24, and 48 hours. Northern blot analysis was carried out to check PCDGF mRNA expression. The upper panel shows PCDGF mRNA expression. The lower panel shows 18S and 28S RNA EB staining to indicate equal loading for each lane.

PCDGF protein expression was also dramatically increased after 48 hour as shown by immunofluorescent staining (FIG. 2). Mouse spleen lymphocytes were incubated at $1.2 \times 10^6$ cells/ml in RPMI 1640 containing 10% FBS for 48 hours without (A) or with (B) 10 μg/ml LPS. Cytospin preparation of cells were fixed with 2% paraformaldehyde in PBS, permeabilized with 0.2% Triton X 100 in PBS, and stained with purified rabbit anti-human PCDGF antibody and developed with Alexia 488-conjugated goat anti-rabbit IgG P (ab') 2. Immunofluorescent staining was observed and photographed using a Olympus BX40 fluorescence microscope equipped with 100 W mercury lamp.

Thymidine incorporation reached a 100 fold stimulation and maximal cpm after 48 hour incubation with 10 μg/ml LPS (FIG. 3). Mouse spleen lymphocytes were cultured at $1.2 \times 10^6$ cells/ml with or without LPS (10 μg/ml) in a final volume of 0.2 ml RPMI 1640 medium containing 10% FBS in flat-bottom 96-well plates. [$^3$H] TdR (1 μCi/well) was added to the culture for the last 6 hours. Thymidine incorporation was checked at 24, 48, and 72 hours. The result are expressed as mean±SD. These data indicated that upon normal B cell activation, PCDGF mRNA and protein expressions were dramatically stimulated.

EXAMPLE 2

PCDGF Expression Increase was Specific to B Cell Activation

Mouse spleen lymphocytes, the cells we used in our experiments, are a mixture of mouse B and T cells. In order to check whether the increase of PCDGF expression is specific to B cell activation, we used Con A, a strong T lymphocyte activator, to stimulate mouse spleen lymphocytes T cells and measure PCDGF expression. As indicated by RT-PCR (FIG. 4), PCDGF mRNA was only detected in LPS stimulated samples but not in control and ConA stimulated samples from 6 to 48 hours. Mouse spleen lymphocytes were incubated at $1.2 \times 10^6$ cells/ml in RPMI 1640 containing 10% FBS with 10 μg/ml LPS, 2.5 μg/ml ConA, or vehicle. RNAs were isolated at 0, 6, 12, 24, and 48 hours and RT-PCR was carried out to check the PCDGF mRNA expression (upper panel). The mouse β-actin was used as a internal control to indicate the equal loading of each lane (lower panel).

PCDGF protein expression was also only detected in LPS stimulated sample (FIG. 5). Mouse spleen lymphocytes were incubated at $1.2 \times 10^6$ cells/ml in RPMI 1640 containing 10% FBS with 10 μg/ml LPS, 2.5 μg/ml ConA, or vehicle for 24 hours. Culture media containing same amount live cells ($6 \times 10^6$ live cells) were used for immunoprecipitation followed by Western blot analysis to check PCDGF protein expression.

Thymidine incorporation data show that mouse spleen lymphocytes were activated by either LPS or Con A (FIG. 6). Mouse spleen lymphocytes were cultured at $1.2 \times 10^6$ cells/ml with 10 μg/ml LPS, 2.5 μg/ml ConA, or vehicle for 48 hours in a final volume of 0.2 ml RPMI 1640 medium containing 10% FBS in flat-bottom 96-well plates. [$^3$H] TdR (1 μCi/well) was added to the culture for the last 6 hours. The results are expressed as mean±SD. These data showed that PCDGF expression increase was specific to B cell activation.

EXAMPLE 3

PCDGF Positive Cells During LPS Stimulation are Proliferating B Cells

In order to prove that the PCDGF positive cells are proliferating B cells upon LPS stimulation, immunoflorescent staining was carried out using anti-PCDGF antibody, anti-BrdU antibody, and anti-B220 antibody. BrdU is a thymidine analog and is specifically incorporated into DNA during DNA synthesis. Staining of the mouse lymphocytes with anti BrdU-fluorescein antibody showed that the lymphocytes stained positive for PCDGF were positive for BrdU indicating that the cells that expressed PCDGF were proliferating cells (FIG. 7). The B220 antigen is expressed on B lymphocytes at all stages from pro-B through mature B cells. B220 is commonly used as a B cell marker. Staining of the mouse lymphocytes with anti B220-FITC antibody showed that the lymphocytes stained positive for PCDGF were positive for B220 indicating that the cells that expressed PCDGF were B cells (FIG. 8). Mouse spleen lymphocytes were incubated at $1.2 \times 10^6$ cells/ml in RPMI 1640 containing 10% FBS for 48 hours without (A, B, C) or with (D, E, F) 10 μg/ml LPS. Cells were fixed with 2% paraformaldehyde in PBS, permeabilized with 0.2% Triton X 100 in PBS, and stained with B220-FITC (A and D), Dapi (B and E), or purified rabbit anti-human PCDGF antibody followed by goat anti rabbit IgG secondary antibody conjugated with Texas red (C and F). Immunofluorescent staining was observed and photographed using a Olympus BX40 fluorescence microscope equipped with 100 W mercury lamp.

EXAMPLE 4

PCDGF Stimulates Mouse Spleen Cell Proliferation

It is important to investigate whether PCDGF alone or with other B cell mitogens can stimulate resting B cell proliferation. We used the thymidine incorporation to determine the effect of PCDGF, anti IgM, or PCDGF with anti IgM on mouse resting B cell proliferation. As shown in FIG. 9, 200 ng/ml PCDGF, 10 μg/ml anti-IgM, 200 ng/ml with 10 μg/ml anti-IgM stimulated mouse resting B cell proliferation by 2.7, 3.7, and 4.6 folds, respectively, after 72 hour treatment. Mouse spleen lymphocytes were incubated at $5 \times 10^6$ cells/ml for 72 hours with 200 ng/ml PCDGF, 10 μg/ml anti-IgM, or both in a final volume of 0.2 ml RPMI 1640 medium containing 10% FBS in flat-bottom 96-well plates. [$^3$H] TdR (1 µCi/well) was added to the culture for the last 16 hours. The result is expressed as mean±SD.

REFERENCES

1. Ashman, L. K. (1999). The biology of stem cell factor and its receptor C-kit. International Journal of Biochemistry & Cell Biology 31, 1037-1051.
2. Blackman, M. A., Tigges, M. A., Minie, M. E., and Koshland, M. E. (1986). A model system for peptide hormone action in differentiation: interleukin 2 induces a B lymphoma to transcribe the J chain gene. Cell 47, 609-617.
3. Burrows, P. D., and Cooper, M. D. (1997). B cell development and differentiation. Current Opinion in Immunology 9, 239-244.
4. Callard, R. E. (1991). Immunoregulation by interleukin-4 in man. British Journal of Haematology 78, 293-299.
5. Conrad, D. H., Waldschmidt, T. J., Lee, W. T., Rao, M., Keegan, A. D., Noelle, R. J., Lynch, R. G., and Kehry, M. R. (1987). Effect of B cell stimulatory factor-1 (interleukin 4) on Pc epsilon and Fc gamma receptor expression on murine B lymphocytes and B cell lines. Journal of Immunology 139, 2290-2296.
6. Cornall, R. J., Goodnow, C. C., and Cyster, J. G. (1995). The regulation of self-reactive B cells. Current Opinion in Immunology 7, 804-811.
7. Duchosal, M. A. (1997). B-cell development and differentiation. Seminars in Hematology 34, 2-12.
8. Frassanito, M. A., Cusmai, A., Iodice, G., and Dammacco, F. (2001). Autocrine interleukin-6 production and highly malignant multiple myeloma: relation with resistance to drug-induced apoptosis. Blood 97, 483-489.
9. Gearing, A., Thorpe, R., Bird, C., and Spitz, M. (1985). Human B cell proliferation is stimulated by interleukin 2. Immunology Letters 9, 105-108.
10. Hardy, R. R., and Hayakawa, K. (2001). B cell development pathways. Annual Review of Immunology 19, 595-621.
11. Howard, M., Farrar, J., Hilfiker, M., Johnson, B., Takatsu, K., Hamaoka, T., and Paul, W. E. (1982). Identification of a T cell-derived b cell growth factor distinct from interleukin 2. Journal of Experimental Medicine 155, 914-923.
12. Ikuta, K., Uchida, N., Friedman, J., and Weissman, I. L. (1992). Lymphocyte development from stem cells. Annual Review of Immunology 10, 759-783.
13. Jansen, J. H., Fibbe, W. E., Willemze, R., and Kluin-Nelemans, J. C. (1990). Interleukin-4. A regulatory protein. Blut 60, 269-274.
14. Kincade, P. W., Lee, G., Pietrangeli, C. E., Hayashi, S., and Gimble, J. M. (1989). Cells and molecules that regulate B lymphopoiesis in bone marrow. Annual Review of Immunology 7, 111-143.
15. LeBien, T. W. (1998). B-cell lymphopoiesis in mouse and man. Current Opinion in Immunology 10, 188-195.
16. Lu, R., and Serrero, G. (1999). Stimulation of PC cell-derived growth factor (epithelin/granulin precursor) expression by estradiol in human breast cancer cells. Biochemical & Biophysical Research Communications 256, 204-207.
17. Lu, R., and Serrero, G. (2000). Inhibition of PC cell-derived growth factor (PCDGF, epithelin/granulin precursor) expression by antisense PCDGF cDNA transfection inhibits tumorigenicity of the human breast carcinoma cell line MDA-MB-468. Proceedings of the National Academy of Sciences of the United States of America 97, 3993-3998.
18. Lu, R., and Serrero, G. (2001). Mediation of estrogen mitogenic effect in human breast cancer MCF-7 cells by PC-cell-derived growth factor (PCDGF/granulin precursor). Proceedings of the National Academy of Sciences of the United States of America 98, 142-147.
19. May, L. T., Ghrayeb, J., Santhanam, U., Tatter, S. B., Sthoeger, Z., Helfgott, D. C., Chiorazzi, N., Grieninger, G., and Sehgal, P. B. (1988). Synthesis and secretion of multiple forms of beta 2-interferon/B-cell differentiation factor 2/hepatocyte-stimulating factor by human fibroblasts and monocytes. Journal of Biological Chemistry 263, 7760-7766.
20. May, L. T., Santhanam, U., Tatter, S. B., Ghrayeb, J., and Sehgal, P. B. (1989). Multiple forms of human interleukin-6. Phosphoglycoproteins secreted by many different tissues. Annals of the New York Academy of Sciences 557, 114-119; discussion 119-121.
21. Mingari, M. C., Gerosa, F., Carra, G., Accolla, R. S., Moretta, A., Zubler, R. H., Waldmann, T. A., and Moretta, L. (1984). Human interleukin-2 promotes proliferation of activated B cells via surface receptors similar to those of activated T cells. Nature 312, 641-643.
22. Muraguchi, A., Hirano, T., Tang, B., Matsuda, T., Horii, Y., Nakajima, K., and Kishimoto, T. (1988). The essential role of B cell stimulatory factor 2 (BSF-2/IL-6) for the terminal differentiation of B cells. Journal of Experimental Medicine 167, 332-344.
23. Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.
24. Ohara, J., Coligan, J. E., Zoon, K., Maloy, W. L., and Paul, W. E. (1987). High-efficiency purification and chemical characterization of B cell stimulatory factor-1/interleukin 4. Journal of Immunology 139, 1127-1134.
25. Osmond, D. G., Rolink, A., and Melchers, F. (1998). Murine B lymphopoiesis: towards a unified model. Immunology Today 19, 65-68.
26. Ostberg, J. R., Barth, R. K., and Frelinger, J. G. (1998). The Roman god Janus: a paradigm for the function of CD43. Immunol Today 19, 546-550.
27. Parker, D. C. (1993). T cell-dependent B cell activation. Annual Review of Immunology 11, 331-360.
28. Pene, J., Rousset, F., Briere, F., Chretien, I., Bonnefoy, J. Y., Spits, H., Yokota, T., Arai, N., Arai, K., and Banchereau, J. (1988). IgE production by normal human lymphocytes is induced by interleukin 4 and suppressed by interferons gamma and alpha and prostaglandin E2. Proceedings of the National Academy of Sciences of the United States of America 85, 6880-6884.
29. Rosenberg, N., and Kincade, P. W. (1994). B-lineage differentiation in normal and transformed cells and the microenvironment that supports it. Current Opinion in Immunology 6, 203-211.
30. Ryan, D. H., Nuccie, B. L., Ritterman, I., Liesveld, J. L., and Abboud, C. N. (1994). Cytokine regulation of early human lymphopoiesis. Journal of Immunology 152, 5250-5258.
31. Takatsuki, F., Okano, A., Suzuki, C., Chieda, R., Takahara, Y., Hirano, T., Kishimoto, T., Hamuro, J., and Aliyama, Y. (1988). Human recombinant IL-6/B cell stimulatory factor 2 augments murine antigen-specific antibody responses in vitro and in vivo. Journal of Immunology 141, 3072-3077.
32. Vos, Q., Lees, A., Wu, Z. Q., Snapper, C. M., and Mond, J. J. (2000). B-cell activation by T-cell-independent type 2 antigens as an integral part of the humoral immune response to pathogenic microorganisms. Immunological Reviews 176, 154-170.

33. Yokota, T., Otsuka, T., Mosmann, T., Banchereau, J., DeFrance, T., Blanchard, D., De Vries, J. E., Lee, F., and Arai, K. (1986). Isolation and characterization of a human interleukin cDNA clone, homologous to mouse B-cell stimulatory factor 1, that expresses B-cell- and T-cell-stimulating activities. Proc Natl Acad Sci USA 83, 5894-5898.

What is claimed is:

1. A method of increasing proliferation of non-tumorigenic B cells in vitro, comprising:
   administering PC-cell derived growth factor (PCDGF) to said cells in vitro in an amount effective to increase the proliferation of said cells.

2. The method of claim 1, wherein said B cells are obtained from a source selected from the group consisting of peripheral blood, bone marrow, umbilical cord blood, spleen and lymph nodes.

3. The method of claim 1, further comprising: administering a B cell mitogen to said B cells in an amount effective to increase the proliferation of said B cells.

4. The method of claim 1, wherein the proliferation of said cells is increased by at least two-fold.

5. The method of claim 1, wherein the proliferation of said cells is increased by at least three-fold.

6. A method of stimulating growth of hybridoma cells, comprising:
   contacting the cells with PCDGF in an amount effective to stimulate the growth of said cells.

7. A method of maintaining immortalized B cells in vitro, comprising:
   contacting the cells with PCDGF in vitro in an amount effective to maintain said cells.

8. A method of increasing the proliferation of a primary B cell culture in vitro, comprising:
   contacting the said B cell culture with PCDGF in an amount effective to increase proliferation of said cell culture.

* * * * *